US012741009B2

(12) United States Patent
Renault

(10) Patent No.: US 12,741,009 B2
(45) Date of Patent: Sep. 22, 2026

(54) ORAL LIPOSOMAL COMPOSITIONS

(71) Applicant: Jean-Yves Renault, Sceaux (FR)

(72) Inventor: Jean-Yves Renault, Sceaux (FR)

( * ) Notice: Subject to any disclaimer, the term of this patent is extended or adjusted under 35 U.S.C. 154(b) by 356 days.

(21) Appl. No.: 18/263,248

(22) PCT Filed: Jan. 28, 2022

(86) PCT No.: PCT/EP2022/052020
§ 371 (c)(1),
(2) Date: Jul. 27, 2023

(87) PCT Pub. No.: WO2022/162131
PCT Pub. Date: Aug. 4, 2022

(65) Prior Publication Data

US 2024/0108685 A1 Apr. 4, 2024

(30) Foreign Application Priority Data

Jan. 29, 2021 (FR) ...................................... 2100892

(51) Int. Cl.

| | |
|---|---|
| ***A61K 38/14*** | (2006.01) |
| ***A61K 9/00*** | (2006.01) |
| ***A61K 9/127*** | (2025.01) |
| ***A61K 47/24*** | (2006.01) |
| ***A61K 47/28*** | (2006.01) |
| ***A61P 35/00*** | (2006.01) |

(52) U.S. Cl.
CPC ............ *A61K 38/14* (2013.01); *A61K 9/0053* (2013.01); *A61K 9/127* (2013.01); *A61K 47/24* (2013.01); *A61K 47/28* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 4,663,311 | A | 5/1987 | Tenu et al. |
| 5,662,907 | A | 9/1997 | Kubo et al. |
| 5,750,395 | A | 5/1998 | Fikes et al. |
| 6,602,510 | B1 | 8/2003 | Fikes et al. |
| 7,976,301 | B2 | 7/2011 | Vath |
| 2004/0157780 | A1 | 8/2004 | Grey et al. |
| 2014/0050780 | A1 | 2/2014 | Cerundolo et al. |
| 2017/0165200 | A1 | 6/2017 | Dong et al. |

FOREIGN PATENT DOCUMENTS

| | | |
|---|---|---|
| CA | 2 131 442 | 9/1993 |
| CA | 2 117 769 | 7/2003 |
| WO | 93/17702 | 9/1993 |
| WO | 01/41787 | 6/2001 |
| WO | 01/42270 | 6/2001 |
| WO | 01/45728 | 6/2001 |
| WO | 03/06816 | 8/2003 |
| WO | 2007/014754 | 2/2007 |

OTHER PUBLICATIONS

Juszkiewicz et al. International Journal of Molecular Sciences vol. 21, 9559. (Year: 2020).*
Search Report issued in corresponding French Application No. 2100892, Oct. 19, 2021, 2 pages.
International Search Report issued in International Application No. PCT/EP2022/052020, Apr. 29, 2022, 6 pages w/ translation.
Written Opinion issued in International Application No. PCT/EP2022/052020, Apr. 29, 2022, 8 pages.
Tanguay, et al., "In Vivo Modulation of Macrophage Tumoricidal Activity by Oral Administration of the Liposome-encapsulated Macrophage Activator CGP 19835A1", Cancer Research 54, 5882-5888, Nov. 15, 1994.

* cited by examiner

*Primary Examiner* — Katherine Peebles
(74) *Attorney, Agent, or Firm* — Maier & Maier, PLLC

(57) ABSTRACT

The present invention relates to a liposomal composition administered orally, nasally or pulmonary comprising a negatively charged phospholipid, optionally a zwitterionic phospholipid, a sterol, and one or more substance (s) amphiphilic (s) of biological interest, preferably a lipophilic immunostimulant useful for treating and/or preventing any pathology implementing the activation of monocytes and/or macrophages.

5 Claims, 3 Drawing Sheets

ORAL LIPOSOMAL COMPOSITIONS

FIELD OF THE INVENTION

The invention relates to novel oral liposomal compositions and their uses.

BACKGROUND OF THE INVENTION

The therapeutic effect of an administered substance is usually directly related to the amount and rate at which the substance reaches the bloodstream. Many factors affect the ability of the substance to reach systemic circulation, including: the site of entry into the body, the physical form of the substance, the design of the product formulation, the physico-chemical properties of the active substance and excipients, and appropriate absorption of said active substance. The oral administration of a therapeutic substance is the most common form of administration today due to convenience and ease of administration.

Factors which influence the absorption, and therefore the ability of the substance to reach the bloodstream of an orally administered substance are related to the physico-chemical properties of the substance, the physiological factors of the gastrointestinal tract and the characteristics of the dosage form. Conventional oral dosage forms consist of solutions, suspensions, powders, two-part gelatin capsules, soft gelatin capsules, tablets with or without coating.

The present invention relates to a liposomal composition for oral, nasal or pulmonary administration comprising a negatively charged phospholipid, a zwitterionic phospholipid, a sterol, and one or more amphiphilic substance(s) of biological interest, preferably a lipophilic immunostimulant useful for treating and/or preventing any pathology involving the activation of monocytes and/or macrophages (innate immune system).

There are anticancer drugs in the form of liposomes that stimulate the immune system of patients. However, these drugs are most often administered in parenteral forms, in particular by the intravenous route.

One such drug is liposomal mifamurtide, also known as liposomal MTP-PE (muramyl tripeptide phosphatidyl ethanolamine) and marketed as Mepact®.

The mode of administration of this drug is very restrictive for the patient since it is administered once or twice a week, in the form of an intravenous infusion for 1 hour.

In addition, the treatment must be administered under medical supervision, therefore preferably in a hospital. This medication is indicated for the treatment of non-metastatic osteosarcoma.

The term "liposomes" generally refers to uni- or multilamellar lipid structures that can be loaded with therapeutic agents, e.g. the therapeutic agent is encapsulated inside the liposome, and/or the therapeutic agent can be attached in the liposome or incorporated into the lipid bilayer(s). These liposomal formulations have been shown to have increased efficacy over the free drug. For example, a liposomal formulation comprising the *vinca* alkaloid vincristine has been shown to have greater efficacy against leukemic cells, compared to free vincristine, and to exhibit reduced overall toxicity.

Besides their ability to improve the therapeutic efficacy of encapsulated biologically active compounds, liposomes have important advantages such as reducing the effective dose of formulated biologically active substances compared to the use of the same free compounds.

The pharmaceutical issues associated with oral administration of liposomes are: 1) stomach pH, 2) bile salts, and 3) digestive enzymes, primarily lipases.

The unbuffered pH of the stomach can range from 1.5 to 2.5 and can cause chemical instability of the liposomal membrane surface.

Bile salts act as detergents and cause instability of the liposomal bilayer through emulsification. Upon exposure to lipases and other enzymes, polar head groups or acyl chains of phospholipids can be cleaved and thereby rupture the liposomal vesicle.

Degradation of liposomes should be avoided because drugs formulated as liposomes and administered orally must be absorbed as intact, undegraded liposomes into the general bloodstream in order to retain their pharmacological properties.

Degradation of liposomes also leads to variability in the absorption of the active ingredient contained in the liposomes. This variability in the absorption of the active principle is a problem since the proportion of active principle absorbed after oral administration must be controlled and reasonably predictable.

The state of the art has already proposed several types of liposomes containing different combinations of lipids with or without lipophilic immunostimulant.

However, the state of the art has not disclosed sufficiently stable liposomal formulations in the presence of bile salts and optionally in an acid and enzymatic medium simulating the gastrointestinal environment, to ensure effective treatment when a liposomal formulation containing one or more amphiphilic substance(s) of biological interest, preferably a lipophilic immunostimulant, is administered orally.

For example, document WO2007014754 describes a composition consisting of one or more amphiphilic substance(s) of biological interest, preferably a lipophilic immunostimulant and a combination of phospholipids, in the presence of cholesterol, useful for the in vivo activation of the immune system. This document specifically describes a composition containing MTP-PE (muramyl tripeptide phosphatidyl ethanolamine), and comprising 62.5% palmitoyl-oleoyl-phosphatidylcholine (POPC), 26.8% di-oleoyl-phosphatidylserine (DOPS) and 10, 7% cholesterol. This document describes the preparation of tablets consisting of Avicel, polyvinylpyrollidone and lyophilizate of a liposomal composition comprising a synthetic lipopeptide, 70% POPC and 30% DOPS.

Another document describes the in vivo biological activity of the synthetic muramyl tripeptide, CGP 19835A, when encapsulated in phosphatidylcholine liposomes (POPC-19835A) and administered orally as an immunomodulator to mice. The liposomes were rapidly absorbed in the intestine and reached the systemic circulation within 4 h. Alveolar macrophages harvested from the lungs of mice 24 h after a single feeding of POPC-19835A were tumoricidal against target cells of murine renal carcinoma (S. Tanguay et al., Cancer Res. 1994 Nov. 15; 54(22):5882-8)

Thus, despite the existence of several liposomal compositions that can be administered orally, there is still a need for new liposomal compositions.

which can be administered orally, containing one or more amphiphilic substance(s) of biological interest, the stability of which is improved in the presence of bile salts.

BRIEF OVERVIEW OF THE INVENTION

In this context of a search for new improved therapeutic compositions, a first object of the invention is to propose a new liposomal composition. A second object of the invention is to provide a method for producing said liposomal composition. Finally, another object of the invention is to provide pharmaceutical compositions and their uses.

DETAILED DESCRIPTION OF THE INVENTION

The applicant of the present invention has therefore shown that a liposome comprising a negatively charged phospholipid, a zwitterionic phospholipid, a sterol in certain ranges in % by weight or by mole and one or more amphiphilic substance(s) of biological interest, preferably a lipophilic immunostimulant useful for the activation of the immune system, in particular the activation of cells of the monocyte or macrophage type, has an improved stability at acid pH and/or in the presence of bile salts.

The present invention thus relates more particularly to a liposomal composition useful for oral administration consisting of or comprising:

a) one or more amphiphilic substance(s) of biological interest, preferably a lipophilic immunostimulant, even more preferably 0, 1 to 10% by weight of the lipophilic derivative of Muramyl di or tri peptide (MDP or MTP), relative to the total weight of the liposomal composition;

b) a liposome consisting of or comprising:

i) from 25% to 35% by weight or by mole of at least one negatively charged phospholipid with respect to the total weight or the total molar weight of the lipids of the liposome, ii) from 30% to 50% by weight or by mole of at least one zwitterionic phospholipid, based on the total weight or the total molar weight of the lipids of the liposome, iii) from 20% to 30% by weight or by mole of at least one sterol, relative to the total weight or the total molar weight of the lipids of the liposome, provided that the at least one zwitterionic phospholipid is neither palmitoyl-oleoyl-phosphatidyl-choline (POPC) nor 1,2-didecanoyl 1-sn-glycero-3-phosphocholine (DDPC).

According to the present invention, the at least one zwitterionic phospholipid is a zwitterionic phospholipid the carbon chain or chains of which is (are) saturated.

According to the present invention, the molar % of constituents i) to iii) concern only the lipids of the liposome, considered as excipients, and do not take into account the lipid part of one or more amphiphilic substance(s) of biological interest, for example lipophilic immunostimulant.

The range of 25% to 35% of at least one negatively charged phospholipid means that the at least one negatively charged phospholipid is present in the liposome at a concentration by weight or mole of preferably 25%, 26%, 27%, 28%, 29%, 30%, 31%, 32%, 33%, 34%, or 35%.

The range of 30% to 50% of at least one zwitterionic phospholipid means that the at least one zwitterionic phospholipid is present in the liposome at a concentration by weight or mole of 30%, 31%, 32%, 33%, 34%, 35%, 36%, 37%, 38%, 39%, 40%, 41%, 42%, 43%, 44%, 45%, 46%, 47%, 48%, 49%, or 50%.

The range of 20% to 30% of at least one sterol means that the at least one sterol is present in the liposome at a concentration by weight or mole of 20%, 21%, 22%, 23%, 24%, 25%, 26%, 27%, 28%, 29%, or 30%.

According to a preferred embodiment, the present invention relates to a liposomal composition of which the liposome consists or comprises, relative to the lipid composition by weight or by total mole of the liposome:

i) from 25% to 35% by weight or by mole of at least one negatively charged phospholipid with respect to the total weight or the total molar weight of the liposome lipids, preferably from 26% to 32%, more preferably 30%, ii) from 30% to 50% by weight or by mole of at least one zwitterionic phospholipid relative to the total weight or to the total molar weight of the lipids of the liposome, preferably from 30% to 40%, more preferably 40%, iii) from 20% to 30% by weight or by mole of at least one sterol relative to the total weight or to the total molar weight of the lipids of the liposome, preferably from 22% to 28%, more preferably 25%, or 30%, characterized in that the said liposomal composition is stable in presence of bile salts, provided that the at least one zwitterionic phospholipid is neither palmitoyl-oleoyl-phosphatidyl-choline (POPC) nor 1,2-didecanoyl 1-sn-glycero-3-phosphocholine (DDPC).

According to the invention, a negatively charged phospholipid must be understood as a phospholipid possessing a negative charge at physiological pH. For example, phosphatidylserine (PS) contains a serine moiety esterified with phosphatidic acid. Due to a single charge on the phosphate group, PS is negatively charged at physiological pH. Phosphatidylinositol (PI) and phosphatidylglycerol (PG) have, respectively, a glycerol group esterified with phosphoric acid or a sugar esterified with phosphoric acid; PI and PG are negatively charged at physiological pH.

More particularly according to the invention, the at least one negatively charged phospholipid is chosen from the group comprising phosphatidylinositol (PI), phosphatidylserine (PS), phosphatidylglycerol (PG), phosphaphatic acid (PA), diphosphatidylglycerol (DPG) or cardiolipin (CL), their derivatives comprising one or more fatty acid residue (s), and mixtures thereof.

According to a preferred embodiment, the at least one negatively charged phospholipid is phosphatidyl serine (PS) or a derivative of phosphatidyl serine chosen from the group comprising palmitoyloleoyl-phosphatidylserine (POPS), palmitoyl-linoeoyl phosphatidylserine (PLPS), palmitoyl-arachidonoyl-phosphatidylserine (PAPS), palmitoyl docosa-hexaenoyl phosphatidylserine (PDPS), stearoyl-oleoyl-phosphatidylserine (OSPS), stearoyl-linoleoyl-phosphatidylserine (GPPS), stearoyl-arachidonoyl-phosphatidylserine (SAPS), stearoyl docosa-hexaenoyl phosphatidylserine (SDPS), di-capryl-phosphatidylserine (C10PS), di-lauroyl-phosphatidylserine (DLPS), di-myristoyl-phosphatidylserine (DMPS), di-phytanoyl-phosphatidylserine (DPhPS), di-heptadecanoyl phosphatidylserine (PS 17:0/17:0), di-oleoyl-phosphatidylserine (DOPS), di-palmitoyl-phosphatidylserine (DPPS), di-stearoyl phosphatidylserine (DSPS), di-linoleoyl phosphatidylserine (di18:3 PS) di-erucoyl phosphatidylserine, di-docosahexaenoyl-phosphatidylserine, and mixtures thereof, preferably dioleoyl phosphatidylserine (DOPS).

According to a preferred embodiment, the at least one negatively charged phospholipid is phosphatidylglycerol or a phosphatidylglycerol derivative chosen from the group comprising palmitoyloleoyl-phosphatidylglycerol, palmitoyl-linoleoyl phosphatidylglycerol, palmitoyl-arachidonoyl-phosphatidylglycerol, palmitoyl-docosahexaenoyl-phosphatidylglycerol, stearoyl-oleoyl-phosphatidylglycerol, stearoyl-linoleoyl-phosphatidylglycerol, stearoyl-arachidonoyl-phosphatidylglycerol, stearoyl-docosahexaenoylphosphatidylglycerol, di-capryl phosphatidylglycerol di-lauroyl phosphatidylglycerol, di-heptadecanoyl-phosphatidylglycerol, di-phytanoyl-phosphatidylglycerol, di-myristoyl phosphatidylglycerol, di-palmitoyl-phosphatidylglycerol (DPPG), di-elaidoyl-phosphatidylglycerol (DEPG), di-stearoyl-phosphatidylglycerol, di-oleoyl-phosphatidylglycerol, di-linoeoyl-phosphatidylglycerol, di-arachidonoyl-phosphatidylglycerol, and mixtures thereof, in particular di-oleoyl-phosphatidylglycerol.

According to the invention, a zwitterionic phospholipid must be understood as a neutral phospholipid at physiological pH. For example, phosphatidylcholine (PC) contains a choline moiety esterified to phosphatidic acid. At physiological pH, PC has both a negative charge carried by the phosphate group and a positive charge carried by the choline group. Phosphatidylethanolamine (PE) contains an ethanolamine group esterified with phosphatidic acid. Since PE has a similar structure to PC, it is also a neutral phospholipid at physiological pH.

More particularly according to the invention, the at least one zwitterionic phospholipid is chosen from the group comprising phosphatidylcholine, phosphatidylethanolamine, their derivatives comprising one or more residue (s) of fatty acid(s), lecithin, lysolecithin, lysophatidyl-ethanolamine, phosphoglycerides, and mixtures thereof.

According to a preferred embodiment, the at least one zwitterionic phospholipid is phosphatidylcholine or a derivative of phosphatidylcholine chosen from the group comprising di-arachidonoyl-phosphatidyl-choline (DAPC), di-elaidoyl-phosphatidyl-choline (DEPC), dilauroyl-phosphatidyl-choline (DLaPC), di-linoleoyl-phosphatidyl-choline (DLPC), di-linolenoyl-phosphatidyl-choline (DLnPC), di-myristoyl-phosphatidyl-choline (DMPC), di-myristoleoyl phosphatidylcholine (DMoPC), dioleoyl phosphatidylcholine (DOPC), di-palmitoyl-phosphatidyl-choline (DPPC), dipentadecanoyl phosphatidyl-choline (DPePC), dipalmitoleoyl-phosphatidyl-choline (DPoPC), diphytanoyl phosphatidyl-choline (DPhPC), di-petroselenoyl-phosphatidyl-choline (DPsPC), di-tridecanoyl phosphatidyl-choline (DTPC), 1-hexadecyl-2-arachidonoyl phosphatidylcholine (HAPC), palmitoyl-arachidonoyl-phosphatidyl-choline (P APC), 1,2-dihexadecanoyl-sn-glycero-3-phosphocholine (DPPC), and 1,2-distearoyl-sn-glycero-3-phosphocholine (DSPC) and mixtures thereof, preferably 1,2-distearoyl-sn-glycero-3-phosphocholine (DSPC) and even more preferably di-myristoyl-phosphatidyl-choline (DMPC).

According to a preferred embodiment, the at least one zwitterionic phospholipid is phosphatidyl-ethanolamine or a derivative of phosphatidyl-ethanolamine chosen from the group comprising palmitoyl-oleoyl-phosphatidyl-ethanolamine, palmitoyllinoleoyl-phosphatidyl-ethanolamine, palmitoyl-arachidonoyl-phosphatidyl-ethanolamine, palmitoyl-docosahexaenoyl phosphatidyl-ethanolamine, stearoyl-oleoyl phosphatidyl-ethanolamine, stearoyl-linoleoyl-phosphatidyl-ethanolamine, stearoyl-arachidonoyl phosphatidyl-ethanolamine, stearoyl-docosahexaenoyl-phosphatidyl-ethanolamine, di-lauroyl phosphatid yl-ethanolamine, di-myristoyl-phosphatidyl-ethanolamine, di-phytanoyl phosphatidyl-ethanolamine, dipalmitoyl phosphatidyl-ethanolamine, diheptadecanoyl phosphatidyl-ethanolamine, distearoyl phosphatidyl-ethanolamine, di-elaidoyl phosphatidyl-ethanolamine, diarachidonoyl phosphatidyl-ethanolamine, docosa-hexaenoyl phosphatidyl-ethanolamine, and mixtures thereof.

According to the invention, the at least one sterol is chosen from the group consisting of cholesterol, cholesterol derivatives such as cholesterol-phosphocholine, cholesterolpolyethyleneglycol and cholesterol-S04, cholesteryl esters, vitamin D, phytosterols, such as sitosterol, campesterol and stigmasterol and mixtures thereof, preferably cholesterol.

According to a preferred embodiment, the present invention relates to a liposomal composition of which the liposome consists or comprises, with respect to the lipid composition by weight or in total mole of the liposome:

i) from 25% to 35% of DOPS, preferably 25%, 26%, 27%, 28%, 29%, 30%, 31%, 32%, 33%, 34%, or 35%, ii) from 30% to 50% of DSPC, DPPC, DMPC, or DLPC preferably 30%, 31%, 32%, 33%, 34%, 35%, 36%, 37%, 38%, 39%, 40%, 41%, 42%, 43%, 44%, 45%, 46%, 47%, 48%, 49%, or 50%, iii) from 20% to 30% cholesterol, preferably 20%, 21%, 22%, 23%, 24%, 25%, 26%, 27%, 28%, 29%, or 30% based on the total weight or the total molar weight of the liposome.

According to a preferred embodiment, the present invention relates to a liposomal composition useful for oral administration consisting of or comprising:

a) one or more amphiphilic substance(s) of biological interest, preferably a lipophilic immunostimulant, even more preferably from 0.1 to 10% by weight of the lipophilic derivative of muramyl di or tri peptide (MDP or MTP), relative to the total weight of the liposomal composition;

b) a liposome consisting of or comprising:

i) from 25% to 35% by weight or by mole of at least one negatively charged phospholipid, preferably 25%, 26%, 27%, 28%, 29%, 30%, 31%, 32%, 33%, 34%, or 35%, relative to the total weight or to the total molar weight of the lipids of the liposome, said at least one negatively charged phospholipid is chosen from the group comprising phosphatidylserine (PS), or a derivative of phosphatidylserine selected from the group consisting of palmitoyl-oleoyl-phosphatidylserine (POPS), palmitoyl-linoleoyl-phosphatidylserine (PLPS), palmitoyl-arachidonoyl-phosphatidylserine (PAPS), palmitoyl-docosa-hexaenoyl-phosphatidylserine (PDPS), stearoyl-oleoyl-phosphatidylserine (OSPS), stearoyl-linoleoyl-phosphatidylserine (GPPS), stearoyl-arachidonoyl-phosphatidylserine (SAPS), stearoyl docosa-hexaenoyl phosphatidylserine (SDPS), di-capryl-phosphatidylserine (ClOP S), di-lauroyl-phosphatidylserine (DLPS), di-myristoyl-phosphatidylserine (ASD), di-phytanoyl-phosphatidylserine (DPhPS), di-heptadecanoyl phosphatidylserine (PS 17:0/17:0), di-oleoyl-phosphatidylserine (DOPS), di-palmitoyl-phosphatidylserine (DPPS), di-stearoyl phosphatidylserine (DSPS), di-linoleoyl phosphatidylserine (di18:3 PS) di-erucoyl phosphatidylserine, di-docosahexaenoyl-phosphatidylserine, and mixtures thereof, preferably di-oleoyl-phosphatidylserine (DOPS), ii) from 30% to 50% by weight or in moles of at least one zwitterionic phospholipid, preferably 30%, 31%, 32%, 33%, 34%, 35%, 36%, 37%, 38%, 39%, 40%, 41%, 42%, 43%, 44%, 45%, 46%, 47%, 48%, 49%, or 50%, based on the total weight or the total molar weight of liposome lipids, iii) from 20% to 30% by weight or by mole of at least one sterol, preferably 20%, 21%, 22%, 23%, 24%, 25%, 26%, 27%, 28%, 29%, or 30%, relative to the total weight or to the total molar weight of the lipids of the liposome, provided that the at least one zwitterionic phospholipid is neither palmitoyl-oleoyl-phosphatidyl-choline (POPC), nor 1,2-didecanoyl 1-sn-glycero-3-phosphocholine (DDPC).

According to a preferred embodiment, the present invention relates to a liposomal composition useful for oral administration consisting of or comprising:

a) one or more amphiphilic substance(s) of biological interest, preferably a lipophilic immunostimulant, even more preferably from 0.1 to 10% by weight of the lipophilic derivative of muramyl di or tri peptide (MDP or MTP), relative to the total weight of the liposomal composition;

b) a liposome consisting of or comprising:

i) from 25% to 35% by weight or by mole of di-oleoyl-phosphatidylserine (DOPS), preferably 25%, 26%, 27%, 28%, 29%, 30%, 31%, 32%, 33%, 34%, or 35%, based on the total weight or the total molar weight of the liposome lipids, ii) from 30% to 50% by weight or by mole of at least a zwitterionic phospholipid, preferably 30%, 31%, 32%, 33%, 34%, 35%, 36%, 37%, 38%, 39%, 40%, 41%, 42%, 43%, 44%, 45%, 46%, 47%, 48%, 49%, or 50%, based on the total weight or the total molar weight of the liposome lipids, iii) from 20% to 30% by weight or by mole of at least one sterol, preferably 20%, 21%, 22%, 23%, 24%, 25%, 26%, 27%, 28%, 29%, or 30%, relative to the total weight or to the total molar weight of lipids in the liposome, provided that the at least one zwitterionic phospholipid is neither palmitoyl-oleoyl-phosphatidyl-choline (POPC) nor 1,2-didecanoyl 1-sn-glycero-3-phosphocholine (DDPC).

According to a preferred embodiment, the present invention relates to a liposomal composition useful for oral administration consisting of or comprising:

a) one or more amphiphilic substance(s) of biological interest, preferably a lipophilic immunostimulant, even more preferably from 0.1 to 10% by weight of the lipophilic derivative of muramyl di or tri peptide (MDP or MTP), relative to the total weight of the liposomal composition;

b) a liposome consisting of or comprising:

i) from 25% to 35% by weight or by mole of di-oleoyl-phosphatidylserine (DOPS), preferably 25%, 26%, 27%, 28%, 29%, 30%, 31%, 32%, 33%, 34%, or 35%, based on the total weight or the total molar weight of the liposome lipids, ii) from 30% to 50% by weight or by mole of at least a zwitterionic phospholipid, preferably 30%, 31%, 32%, 33%, 34%, 35%, 36%, 37%, 38%, 39%, 40%, 41%, 42%, 43%, 44%, 45%, 46%, 47%, 48%, 49%, or 50%, based on the total weight or the total molar weight of the liposome lipids, iii) from 20% to 30% by weight or by mole of cholesterol, preferably 20%, 21%, 22%, 23%, 24%, 25%, 26%, 27%, 28%, 29%, or 30%, relative to the total weight or the total molar weight of the liposome lipids, provided that the at least one zwitterionic phospholipid is neither palmitoyl-oleoyl-phosphatidyl-choline (POPC) nor 1,2-didecanoyl 1-sn-glycero-3-phosphocholine (DDPC).

According to a preferred embodiment, the present invention relates to a liposomal composition useful for oral administration consisting of or comprising:

a) one or more amphiphilic substance(s) of biological interest, preferably a lipophilic immunostimulant, even more preferably from 0.1 to 10% by weight of the lipophilic derivative of muramyl di or tri peptide (MDP or MTP), relative to the total weight of the liposomal composition;

b) a liposome consisting of or comprising:

i) from 25% to 35% by weight or by mole of di-oleoyl-phosphatidylserine (DOPS), preferably 25%, 26%, 27%, 28%, 29%, 30%, 31%, 32%, 33%, 34%, or 35%, based on the total weight or the total molar weight of the liposome lipids, ii) from 30% to 50% by weight or by mole of DSPC, DPPC, DMPC, or DLPC, preferably DSPC and even more preferably DMPC, preferably 30%, 31%, 32%, 33%, 34%, 35%, 36%, 37%, 38%, 39%, 40%, 41%, 42%, 43%, 44%, 45%, 46%, 47%, 48%, 49%, or 50%, relative to the total weight or the total molar weight of the liposome lipids, iii) from 20% to 30% by weight or by mole of at least one sterol, preferably 20%, 21%, 22%, 23%, 24%, 25%, 26%, 27%, 28%, 29%, or 30%, based on the total weight or the total molar weight of liposome lipids.

According to a preferred embodiment, the present invention relates to a liposomal composition useful for oral administration consisting of or comprising:

a) one or more amphiphilic substance(s) of biological interest, preferably a lipophilic immunostimulant, even more preferably from 0.1 to 10% by weight of the lipophilic derivative of muramyl di or tri peptide (MDP or MTP), relative to the total weight of the liposomal composition;

b) a liposome consisting of or comprising:

i) from 25% to 35% by weight or by mole of di-oleoyl-phosphatidylserine (DOPS), preferably 25%, 26%, 27%, 28%, 29%, 30%, 31%, 32%, 33%, 34%, or 35%, based on the total weight or the total molar weight of the liposome lipids, ii) from 30% to 50% by weight or by mole of DSPC, DPPC, DMPC, or DLPC, preferably DSPC and even more preferably DMPC, preferably 30%, 31%, 32%, 33%, 34%, 35%, 36%, 37%, 38%, 39%, 40%, 41%, 42%, 43%, 44%, 45%, 46%, 47%, 48%, 49%, or 50%, relative to the total weight or the total molar weight of the liposome lipids, iii) from 20% to 30% by weight or by mole of cholesterol, preferably 20%, 21%, 22%, 23%, 24%, 25%, 26%, 27%, 28%, 29%, or 30%, based on the total weight or the total molar weight of the liposome lipids.

According to another preferred embodiment, the present invention relates to a liposomal composition of which the liposome consists or comprises, with respect to the lipid composition by weight or by total mole of the liposome:

i) from 25% to 35% by weight or by mole of DOPS, ii) from 30% to 50% by weight or by mole of DSPC, DPPC, DMPC, or DLPC, preferably DSPC and even more preferably DMPC, iii) from 20% to 30% by weight or by mole of cholesterol.

According to another preferred embodiment, the present invention relates to a liposomal composition of which the liposome consists of or comprises with respect to the total lipid composition by weight or by mole of the liposome:

i) 30% DOPS, ii) 40% DSPC, DPPC, DMPC, or DLPC, preferably DSPC and even more preferably DMPC, iii) 30% cholesterol.

According to a preferred embodiment, the liposomes of the liposomal composition are stable in the presence of bile salts, that is to say the lipid bilayer of the liposomes is not de structured.

According to a preferred embodiment, the liposomes of the present liposomal composition are stable in the presence of bile salts for at least 1 hour, preferably 2 hours or 3 hours.

According to a preferred embodiment, the liposomes of the present liposomal composition are stable in the presence of bile salts and are absorbed and transferred to the bloodstream.

A person skilled in the art understands that the therapeutic efficacy of the liposomal compositions of the present invention, administered orally, is conditioned by the stability of said liposomal compositions in a medium comprising bile salts.

According to a preferred embodiment, the therapeutic agent is a lipophilic immunostimulant useful for activating the immune system, for treating and/or preventing cancer, in particular osteosarcoma.

This activation of the immune system is obtained by absorption of the liposomal suspension by immunocompetent cells which are then activated after the binding of the immunostimulating amphiphilic substance to specific receptors. This activation can also be obtained via an initial ex vivo activation step under specific immunocompetent cell culture conditions such as monocytes, macrophages or dendritic cells.

According to a preferred embodiment, the therapeutic agent is a lipophilic immunostimulant belonging to the therapeutic subgroup ATC L03 of the WHO Anatomical, Therapeutic and Chemical Classification, for example interferon or an interferon derivative.

In an advantageous embodiment of the invention, an amphiphilic substance of biological interest or at least one of the amphiphilic substances of biological interest according to the invention is a selected amphiphilic immunostimulant.

In an advantageous embodiment of the invention, the amphiphilic immunostimulant is combined with amphiphilic peptides or with lipopeptide antigens.

The combination of an amphiphile immunostimulant and one or more amphiphile peptides or lipopeptide antigens is designed to also induce specific immune responses to the amphiphile peptides or lipopeptide antigens.

The expression "amphiphilic immunostimulant" refers to all substances capable of triggering innate immune responses via receptors such as the TOLL and NOD receptors of monocytes, macrophages, dendritic cells, NK cells or polynuclear cells, in vitro or in vivo, and capable to be anchored, by its lipid part, in the lipid bilayers of a liposome. Examples of amphiphilic immunostimulants are muramyl tripeptide phosphatidyl ethanolamine (MTP-PE), bis-(taurine)-L-glutaminyl-N-palmitoyl-S-[2-(R)-3-dilauroyl oxypropyl]-L-cystine (JBT 3002), sitosterol, lipid A or other LPS derivatives or nucleotides rich in amphiphilic CpG motifs. The present invention is not limited to the amphiphilic immunostimulants described above.

In a particular embodiment of the present invention, the amphiphilic immunostimulant is muramyl tripeptide phosphatidyl ethanolamine (MTP-PE).

Muramyl tripeptide phosphatidyl ethanolamine has been described as an adjuvant for studies of protection against tumor antigens or virus antigens (virus of herpes simplex or HIV-1). MTP-PE has a stimulating effect on cell proliferation and is able to activate the cytotoxic abilities of monocytes.

In another particular embodiment of the present invention, the amphiphilic immunostimulant is bis-(taurine)-L-glutaminyl-N-palmitoyl-S-[2-(R)-3-dilauroyloxypropyl]-L-cystine (JBT3002), a synthetic bacterial lipopeptide capable of activating macrophages and inducing the production of inflammatory cytokines (TNF-[alpha], IL-I, IL-6).

In another particular embodiment of the present invention, the amphiphilic immunostimulant is sitosterol. By sitosterol is meant sitosterol, as well as [omicron] eta-sitosterol, [omicron] eta-sitosterol glucoside. The immunostimulatory capacity of 6eta-sitosterol (a phytosterol) has been demonstrated in vitro and in vivo. [epsilon] eta-sitosterol is able to enhance T cell proliferation in the presence of phytohemagglutinin, stimulate NK cell activity and induce increased secretion of IL-2 and interferon gamma by lymphocytes.

The amphiphilic immunostimulants described above can be associated with amphiphilic peptides or with lipopeptide antigens. Said amphiphilic peptides or lipopeptide antigens are preferably formed by peptide chains of 8 to 16 amino acids (considered as immunogenic peptides), linked via the NH2 terminal group to an aliphatic and lipid chain of 5 to 30 carbons, more preferably 8 at 18 carbons. The typical immunogenic peptides used are selected from wild-type or modified peptide antigens having a high affinity for MHC class I and MHC class IL molecules. Said peptides can be selected from the group consisting of peptides inducing CTL, peptides d tumor cell antigen or hepatitis antigen peptides. More preferably, the peptides are chosen from the group consisting of carcinoma solid tumor cell antigens (WO 0142270, U.S. Pat. No. 6,602,510, WO 0145728 and U.S. Pat. No. 07,976,301), melanoma antigens (U.S. Pat. Nos. 5,662,907 and 5,750,395), hepatitis B or C antigens or other tumor antigens such as 5T4 breast cancer antigens (WO 03068816), Her2/neu antigens (US 2004/157780) or p53 antigens (WO 00141787).

According to a preferred embodiment, the therapeutic agent is a lipophilic immunostimulant derived from lipopolysaccharide (LPS).

According to a preferred embodiment, the therapeutic agent is a combination of several lipophilic immunostimulants.

According to a preferred embodiment, the therapeutic agent is a lipophilic derivative of Muramyl di or tri peptide (MDP or MTP).

In another preferred embodiment, the lipophilic derivative of MTP corresponds to the formula (I) or (II)

(I)

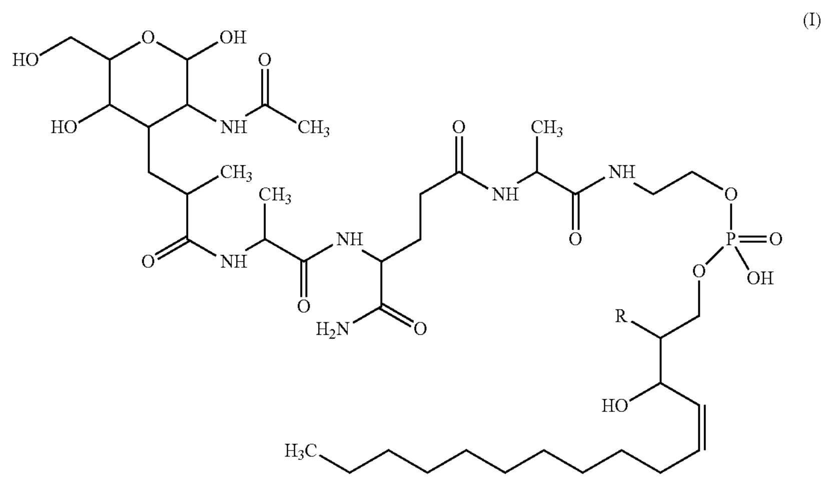

wherein

R represents an —NH2 group, or a —NH—CO—R1 group where R1 represents an acid residue fatty $C_5$-$C_{24}$ or a linear or branched alkyl group, $C_1$-$C_{30}$, optionally having one or more carbon-carbon double bonds, preferably a $C_8$-$C_{18}$ alkyl group, optionally having one or more carbon-carbon double bonds.

In another preferred embodiment, R1 is selected from a residue of caprylic acid (8:0), capric acid (10:0), lauric acid (12:0), myristic acid (14:0) palmitic acid (16:0), stearic acid (18:0), arachidic acid (20:0), behenic acid (22:0), lignoceric acid (24:0), cerotic acid (26:0), myristoleic acid (14:1), palmitoleic acid (16:1), sapienic acid (16:1), oleic acid (18:1), elaidic acid (18:1), trans-vaccenic acid (18:1), linoleic acid (18:2), linolelaic acid (18:2), a-linolenic acid (18:3), y-linolenic acid (18:3), dihomo-y-linolenic acid (20:3), arachidonic acid (20:4), eicosapentaenoic acid (20:5), clupanodonic acid (22:5), or docosahexaenoic acid (22:6); or In a preferred embodiment the lipophilic immunostimulant is MTP-PE (mifamurtide). This muramyl tripeptide comprises phospholipid residues which allow the association of the hydrophobic part of the molecule with a lipid environment while the muramyl peptide part associates with the aqueous environment.

Muramyl tripeptide phosphatidyl ethanolamine has been described as an adjuvant for studies of protection against tumor antigens or viral antigens (Herpes simplex virus or HIV-1). MTP-PE has a stimulating effect on cell proliferation and is able to activate the cytotoxic abilities of monocytes.

Mifamurtide is marketed as Mepact® and is indicated in patients aged two to 30 years for the treatment of high-grade non-metastatic osteosarcoma (a type of bone cancer). Mepact® is used in combination with other anti-cancer medicines after surgical removal of cancer.

According to the summary of the European Public Assessment Report (EPAR) for Mepact®, the use of mifamurtide (II)

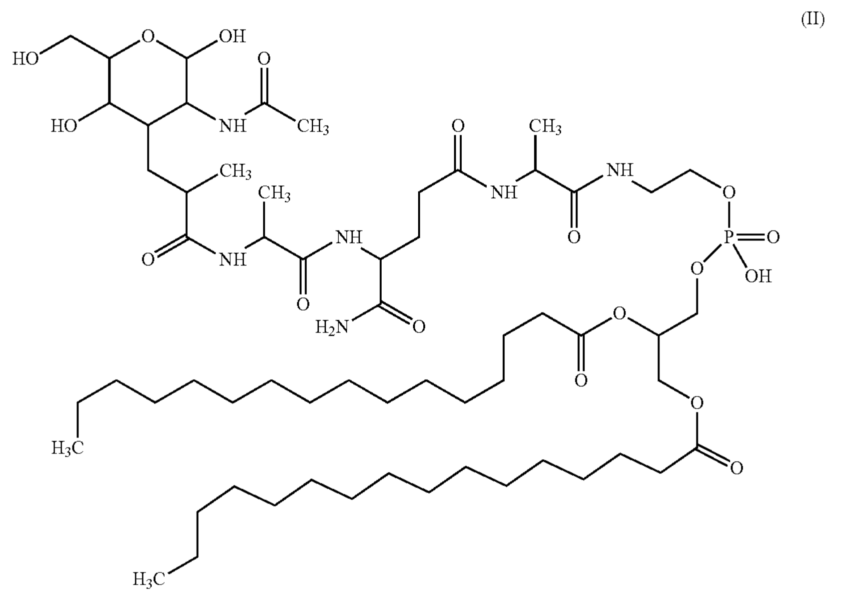 [SMILES: CCCCCCCCCCCCCCCC(=O)OCC(COP(=O)(O)OCCNC(=O)C(C)NC(=O)CCC(NC(=O)C(C)NC(=O)C(C)CC1C(O)C(CO)OC(O)C1NC(C)=O)C(N)=O)OC(=O)CCCCCCCCCCCCCCC]

in combination with other anticancer medicinal products increases the duration of patient survival without disease recurrence: 68% of patients on Mepact® (231 of 338) survived without disease recurrence, compared to 61% of patients (207 of 340) who did not receive it.

The risk of death was also reduced by 28% in patients taking Mepact®.

This treatment is injected by infusion.

The recommended mifamurtide dose for all patients is 2 mg/m2 body surface area.

It should be administered twice a week at least 3 days apart for 12 weeks, then once a week for a further 24 weeks, for a total of 48 infusions over 36 weeks.

After intravenous infusion of Mepact®, the liposomes are selectively taken over by macrophages, phagocytosed and progressively degraded in the cells.

Side effects seen with Mepact® (in more than 1 in 10 patients) are: anemia (low red blood cell count), loss of appetite, headache, dizziness, tachycardia (rapid heartbeat), high blood pressure (high blood pressure), hypotension (low blood pressure), dyspnea (difficulty breathing), tachypnea (fast breathing), cough, vomiting, diarrhoea, constipation, abdominal pain (stomach ache), nausea, hyperhidrosis (excessive sweating), myalgia (muscle pain), arthralgia (pain in joints), back pain, pain in extremities (arms and legs), fever, chills, fatigue, hypothermia (low body temperature), general pain, malaise, asthenia (weakness) and pain in the chest.

The antimetastatic properties of Mepact® have also been shown in clinical studies (Kleinerman et al. American Journal of Clinical Oncology 1995, 18(2): 93-9. Anderson et al. Pediatric Blood & Cancer 2014, 61(2): 238-44).

The Mepact® liposomal composition contains 0.4% (4 mg of mifamurtide). The liposome consists of 1-Palmitoyl-2-oleoyl-sn-glycero-3-phosphocholine (POPC) and 1,2-dioleoyl-sn-glycero-3-phospho-L-serine (DOPS) according to the molar ratio 7:3.

According to a preferred embodiment, the present invention relates to a liposomal composition, the lipophilic immunostimulant of which consists of or comprises a concentration of 0.1 to 10% by weight of the lipophilic derivative of Muramyl di or tri peptide (MDP or MTP), preferably 0.4% or less by weight of MTP-PE.

According to another preferred embodiment, the present invention relates to a liposomal composition, consisting of or comprising:

a) from 0.1 to 1% by weight of the lipophilic derivative of Muramyl di or tri peptide (MDP or MTP), preferably 0, 4% or less by weight of MTP-PE, b) a liposome consisting of or which comprises with respect to the total lipid composition by weight or by mole of the liposome:

i) from 25% to 35% of a phosphatidylserine, preferably DOPS, preferably from 26% to 32%, more preferably 30%, ii) from 30% to 50% of a phosphatidylcholine, preferably DSPC, DPPC, DMPC, or DLPC, preferably from 30% to 40%, more preferably 40%, iii) from 20% to 30% of at least one sterol, preferably cholesterol, preferably from 22% to 28%, more preferably 25%, or 30%.

According to another preferred embodiment, the present invention relates to a liposomal composition, consisting of or comprising:

a) from 0.1 to 10% by weight of the lipophilic derivative of Muramyl di or tri peptide (MDP or MTP), preferably 0, 4% or less by weight of MTP-PE, b) a liposome consisting of or which comprises with respect to the lipid composition by weight or in total mole of the liposome:

i) 30% of DOPS, ii) 40% of DSPC, DPPC, DMPC, or DLPC, preferably DSPC and even more preferably DMPC, iii) 30% cholesterol.

According to another preferred embodiment, the present invention relates to a liposomal composition for the preparation of a pharmaceutical composition intended for oral administration.

Oral administration means administration by ingestion of tablets, pills or capsules containing the powder according to the invention.

Oral administration also refers to administration of a suspension of the powder in a pharmaceutically acceptable aqueous solvent, for example in the form of a syrup or an oral suspension.

According to another preferred embodiment, the present invention relates to a liposomal composition for the preparation of a pharmaceutical composition administered by the nasal route.

According to another preferred embodiment, the present invention relates to a liposomal composition for the preparation of a pharmaceutical composition administered by the pulmonary route.

According to another preferred embodiment, the present invention relates to a liposomal composition for its use in a method for activating the innate immune system, in particular the activation of cells of the monocyte or macrophage type.

A person skilled in the art understands that the activation of the immune system, in particular the activation of cells of the monocyte or macrophage type, makes it possible to treat cancers and in particular cancerous metastases.

According to a particular embodiment of the invention, the present liposomal composition is used for the treatment of patients suffering from cancer, preferably osteosarcoma, kidney cancer or cancer of the mammary gland.

According to a particular embodiment of the invention, the present liposomal composition is used for the treatment and/or the prevention of cancerous metastases, in particular pulmonary metastases.

The present invention also relates to a method for treating cancers or preventing cancer recurrences, in particular cancers of the bones, kidney or mammary gland and their metastases, in particular pulmonary, using a liposomal composition described above.

Preparation of Liposomes

The liposomes of the present invention are prepared according to techniques known to those skilled in the art. For example, this preparation method is based on two separate solubilization steps, in which the lipids are solubilized in a water-miscible polar solvent (tertiary butanol hereafter also called t-butanol) or a mixture of chloroform and of methanol (in the proportions 5:1) (solution A) and the biologically active agent is dispersed in a physiologically compatible aqueous medium optionally containing a cryoprotectant (solution B).

Solution A and solution B are then mixed together. Consequently, according to this method, the amphiphilic substance of biological interest is initially not present in the t-butanol phase but only in the aqueous medium.

Alternatively, the lipids and the biologically active agent are directly mixed in a water-miscible polar solvent.

Document WO2007014754 describes another method which is particularly suitable for the preparation of the liposomes according to the present invention.

This process, which comprises a dispersion step (followed by a lyophilization or atomization/drying step) of phospholipids, and of cholesterol, and of one or more amphiphilic substances of biological interest in an appropriate mixture of solvents, allows the production of a liposomal suspension.

More particularly, the process for preparing the liposomal suspension comprises:

a) a step of preparing a mixture of a lipophilic immunostimulant and a liposome consisting of or which comprises, relative to the lipid composition by weight or in total mole of the liposome:

i) from 25% to 35% of at least one negatively charged phospholipid, ii) from 30% to 50% of at least one zwitterionic phospholipid, iii) from 20% to 30% of at least one sterol, b) a step of dispersing said mixture in a miscible polar solvent at the water.

According to a particular embodiment, the polar solvent consists of t-butanol dihydrate and t-butanol or a mixture of chloroform/methanol in particular in a 5:1 ratio.

The polar solvent can also consist of a mixture of 60 to 100% t-butanol dihydrate and 0 to 40% t-butanol, preferably in a mixture of 75% to 100% (w/w) of t-butanol dihydrate and 0-25% (w/w) t-butanol.

The invention also relates to a method for preparing a powder according to the invention, comprising a step c) of atomizing/drying the liposomal suspension obtained in step b).

According to a particular embodiment, the liposomal suspension contains a hydrophilic excipient, preferably mannitol added before the atomization/drying step.

According to another aspect of the invention the liposomal suspension is extruded through a porous device and then passed through a nozzle. Use of a sufficiently small diameter nozzle restricts the flow of the suspension after it has been extruded through the porous device.

Useful nozzles for carrying out this step of the method of the invention are also generally known to those skilled in the art. They include, for example, rotating disc nozzles, impact jet nozzles, capillary nozzles, single orifice nozzles, vibrating or pulsating type ultrasonic nozzles, two-fluid nozzles such as nozzles two-fluid coaxial, etc. In a preferred embodiment of the invention, the nozzle is an orifice nozzle. In the present invention, the preferred pore size of the nozzle is between about 0.05 mm and about 1 mm, more preferably between about 0.1 mm and about 0.2 mm.

In the device of the invention, the nozzle can be included in a container suitable for dehydrating the liposome obtained, in particular suitable for dehydration by atomization or by atomization.

The flow rate of the suspension can be between about 1 ml/min and about 1000 ml/min. More typically, liposomes were prepared by the method of the invention applying a flow rate of 10 ml/min to 200 ml/min, and more preferably from about 20 ml/min to about 100 ml/min.

According to another embodiment, the pressure used for the extrusion of the liposomal suspension through the porous device and the passage pressure of the liposomal suspension through the nozzle can be substantially identical, in particular be between 0.5 bar and 1200 bar. More typically, liposomes can be prepared by the method of the invention with 5 bar to 600 bar, preferably from about 10 bar to about 500 bar, and more preferably from about 20 bar to about 150 bar.

The drying of the liposomes after the formation of droplets can be carried out by bringing the droplets into contact with a gas stream, preferably a heated gas stream, to obtain solid particles. Preferably, the gas stream used is an inert gas. The drying gas may preferably be a low oxygen gas containing less than 0.1 vol. %, preferably less than 0.05 vol. % oxygen. Inert gases increase the safety of a heated drying system. In a preferred embodiment of the invention, nitrogen is used as the inert gas. In another embodiment of the invention, the inert gas protects the active ingredients and the excipients contained in the formulation. Preferably, the spray drying is carried out in a device suitable for spray drying.

Spray drying can for example be carried out in a drying tower. The dehydrated liposomes are separated from the gas stream and collected.

In a preferred embodiment, the liposomal suspension optionally includes a hydrophilic excipient. Useful hydrophilic excipients can be monomers, oligomers or polymers and can be found among several chemical classes of compounds.

According to one of the preferred embodiments of the invention, the hydrophilic excipient is a saccharide, e.g. a mono-, di-, oligo- or polysaccharide, sugar alcohol, amino acid, peptide, protein, water-soluble polymer or a combination thereof.

A saccharide, or carbohydrate, is defined as a compound primarily composed of carbon, hydrogen, and oxygen. Useful saccharides include sugars and sugar alcohols, oligosaccharides, water-soluble polysaccharides and their derivatives. Preferred saccharides according to the invention include, but are not limited to, glucose, fructose, lactose, sucrose, trehalose, maltose, cellobiose, galactose, maltotriose, maltopentose, raffinose, dextrin, dextran, inulin, mannitol, sorbitol, xylitol, chitosan; water-soluble cellulose derivatives such as methylcellulose, hydroxypropylcellulose, hydroxyethylcellulose and hypromellose; alginates, soluble starches or starch fractions, xanthan gum, guar gum, pectin, carrageenan, galactomannan, gellan gum, tragacanth gum, including any derivative thereof. Particularly preferred saccharides are glucose and trehalose.

Other useful hydrophilic excipients can be chosen from other chemical classes, such as water-soluble amino acids, peptides or proteins. For example, glycine or other natural amino acids can be used. Useful proteins include, but are not limited to, gelatin, albumin, whey protein, soy protein, or other food or plant proteins.

Other examples of useful hydrophilic excipients are polymers such as water-soluble polymers such as solid polyethylene glycols, polyvinyl alcohol, polyacrylates or polyvinylpyrrolidone.

According to the invention, mixtures of more than one hydrophilic excipient can be used. For example, it may be necessary to independently adjust several parameters such as pH, solubility and wettability. In this case, a first hydrophilic excipient can be chosen as the basic carrier material for the colloidal systems, while one or more additional hydrophilic excipients can be incorporated to obtain a certain pH and/or wettability.

Of course, the aqueous medium comprising the liposomal suspension can comprise other excipients or auxiliary, hydrophilic or water-soluble substances. These substances are soluble and extracted by the extraction medium or not, these substances can be included in the dry particles or eliminated with water and the organic solvent. The substances, which are included in the dry particles, must be pharmaceutically acceptable.

Other preferred excipients include stabilizers, surfactants, wetting agents, bulking agents, lyophilization aids, antioxidants, chelating agents, preservatives, osmotic agents, acidic or alkaline excipients to adjust the pH, etc.

Among the preferred excipients according to the invention are stabilizers and antioxidants. Antioxidants can prevent the oxidation of an incorporated active compound, but also that of the components of the colloid, in particular if oxidation-sensitive lipids are used. Useful compounds include, for example, fat-soluble antioxidants such as alpha, beta and gamma-tocopherol, ubiquinol, lycopene, alpha and beta-carotene, nordihydroguaiaretic acid, butyl hydroxyanisole, butyl hydroxytoluene, ethylenediamine tetraacetic acid, dienta-etriamine pentaacetic acid, etc. Alpha-tocopherol and ethylenediaminetetraacetic acid are particularly preferred, including their pharmaceutically acceptable derivatives. On the other hand, if chemically pure, semi-synthetic or synthetic saturated lipids are used for the composition of the colloidal systems, no antioxidant may be necessary.

The invention also relates to a powder described above such as that prepared by a process comprising steps a-c), said powder consisting of or comprising a liposome consisting of or which comprises, relative to the lipid composition by weight or in total mole of the liposome:

i) from 25% to 35% of at least one negatively charged phospholipid,
ii) from 30% to 50% of at least one zwitterionic phospholipid,
iii) from 20% to 30% of at least one sterol,
iv) from 0.1 to 10% by weight of the lipophilic derivative of Muramyl di or tri peptide (MDP or MTP).

The invention also relates to a process for the preparation of liposomes with a size and size distribution suitable for oral administration.

Preferably, the liposomes of the composition of the present invention can have a diameter of between 100 nm and 10 μm, preferably 1 to 10 μm and more preferably 2 to 5 μm. The diameter of the liposomes can be controlled, for example, by extruding the liposomal composition through a polycarbonate filter having a known pore size. Methods for controlling the size of liposomes are well known in the art and are described, for example, in Mayhew et al. (1984) Biochem. Biophys. Acta.

It is possible to determine the average particle size of the liposomes.

Indeed, a particle size distribution is characterized by the mean values (mean values): mean diameter number (NMD), mean volume diameter (VMD) and the polydispersity in size is generally characterized by the VMD/NMD ratio (poly dispersity index, IP).

A value of 1.00 or close to 1.00 means that all particles are the same size, the greater the deviation from 1.00, the higher the size polydispersity.

The particle size distribution can be determined by the NANOTRAC technique based on the analysis of the Brownian motion of the particles dispersed in a liquid by acquisition of the energy spectrum corresponding to the Doppier shift.

The MTUPA 250-NANOTRAC 250 device, equipped with a 780 nm laser, operates by laser scattering for particles of size from 0.8 to 6500 nm.

The liposomes obtained according to the present invention are characterized by a polydispersity of 1.00 to 1.20.

Liposomes, dry particles or a powder comprising them, as obtained by the method of the invention, can be used in the manufacture of a medicament.

If the particles meet all the requirements of a pharmaceutical dosage form, they can be used as such and introduced directly into suitable containers.

The powder containing the liposomes may contain residual water (0.1 to less than 5%), closely bound to the lipids, resulting from the process for preparing said powder.

Alternatively, the powder containing the liposomes can be mixed with other active and/or inactive ingredients such as pharmaceutically acceptable carriers.

According to a particular embodiment, the powder is micronized to an average size of between 1 and 5 micrometers, suitable for administration by inhalation.

For application by inhalation, the powder according to the invention is loaded into a dry spray device to deliver said powder in the form of an aerosol.

Said dry spraying device makes it possible to deposit said powder for example in the throat, on the tonsils, or advantageously directly in the pulmonary alveoli where the resident macrophages can be directly activated by the liposomal suspension formed in situ.

The invention also relates to a liposomal suspension, preferably multi-lamellar, obtained by bringing a powder according to the invention into contact with an aqueous medium.

The aqueous medium may be sterile water, optionally buffered to pH 7.0-7.5 and optionally containing preservatives or antioxidants.

The invention also relates to the use of a multi-lamellar liposomal powder or suspension according to the invention for the in vivo activation of the immune system.

This activation of the immune system is obtained by absorption of the liposomal suspension by immunocompetent cells which are then activated after the binding of the immunostimulating amphiphilic substance to specific receptors.

This activation can also be obtained via an initial ex vivo activation step under specific immunocompetent cell culture conditions such as monocytes, macrophages or dendritic cells.

In a preferred embodiment, the pharmaceutical composition according to the invention contains the powder present in a range of 50 mg to 2 g in a single application or unit.

The liposomes of the present invention are stable in the presence of bile salts.

According to the present invention, the term "stable liposome in the presence of bile salts" means a liposome, dispersed in an aqueous medium, the lipid bilayer of which is not destructured by treatment with bile salts, preferably in the presence of taurocholate sodium, sodium deoxycholate and sodium cholate hydrate or their mixtures, preferably a mixture containing the three bile salts.

The liposome stability test is carried out in the presence of bile salts at a concentration of 2 to 10 mM each, preferably 4 mM. The test is carried out at an ambient temperature of 20° C. or 37° C. The liposomes are brought into contact with the bile salts for at least 1 hour, preferably 2 hours or 3 hours.

The stability of the liposomes after treatment in the presence of bile salts is demonstrated by a visual test. Indeed, the suspension of liposomes before treatment appears slightly opaque with a whitish color; when the liposomes are denatured by bile salts, the suspension of denatured liposomes is transparent. Observation under an optical microscope shows liposome debris (see FIG. 6).

The present invention is further illustrated, but not limited to, by the following figures and examples.

LIST OF FIGURES

EXPERIMENTAL PART

Figure 1:
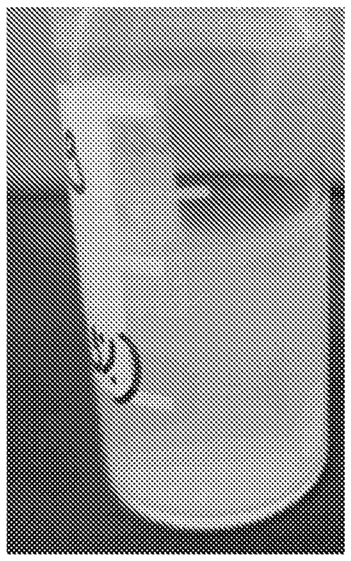
FIG. 1 shows a vial containing a liposome suspension before treatment with bile salts.

Example 1: Manufacture and Analysis of Liposomal MTP-PE Suspensions

The following reagents were used (suppliers are indicated in brackets): MTP-PE (or mifamurtide, Sigma-Aldrich), methanol (VWR Chemicals), ethanol (Sigma-Aldrich), chloroform (Sigma-Aldrich), dichloromethane (Carlo Erba), acetonitrile (VWR Chemicals), acetone (Sigma-Aldrich), ethyl acetate (Carlo Erba), tetrahydrofuran (VWR Chemicals), dimethylsulfoxide (Honey Well), trifluoroacetic acid (VWR Chemicals), ammonium formate (Fluka), 2-oleoyl-1-palmitoyl-sn-glycero-3-phosphocholine or POPC (Lipoid), 1,2-dioleoyl-sn-glycero-3-phospho-L-serine or DOPS, as the sodium salt (Avanti Polar Lipids), cholesterol (Sigma-Aldrich), 1,2-didecanoyl-sn-glycero-3-phosphocholine or DDPC (Lipoid), 1,2-dilauroyl-sn-glycero-3-phosphocholine or DLPC (Lipoid), 1,2-dimyristoyl-sn-glycero-3-phosphocholine or DMPC (Lipoid), 1,2-dipalmitoyl-sn-glycero-3-phosphocholine or DPPC (Lipoid) and 1,2-distearoyl-sn-glycero-3-phosphocholine or DSPC (Lipoid).

Method: The lipids and mifamurtide were dissolved in a mixture of chloroform and methanol (5:1), at a concentration of approximately 30 mg/mL, then concentrated by drying in a rotary evaporator (2 hours at 40° C.) to form a lipid film.

The lipid film was then rehydrated in an aqueous saline solution (0.9% NaCl, 5 mL) at room temperature and with magnetic stirring.

The suspension obtained was then filtered 10 times through a 5 μm polycarbonate membrane using an Avanti Polar Mini-Extruder to obtain a liposomal suspension.

Several types of liposomes, containing 0.4% of MTP-PE (ie 1 mg of mifamurtide for 250 mg of lipids), were prepared using variable proportions of lipids (expressed in %)

TABLE 1

| Suspension No. (code used in the laboratory) | DOPS | Phospholipide zwitterionique | Cholesterol |
|---|---|---|---|
| No1 (Tanguay) | | POPC 100% | |
| No2 (Mepact) | 30% | POPC 70% | |
| No3 (HPX-0) | 30% | POPC 40% | 30% |
| No4 (HPX-1) | 30% | DSPC 70% | |

TABLE 1-continued

| Suspension No. (code used in the laboratory) | DOPS | Phospholipide zwitterionique | Cholesterol |
|---|---|---|---|
| No5 (HPX-2) | 30% | POPC 30% | 40% |
| No6 (HPX-3) | 30% | DSPC 30% | 40% |
| No7 (HPX-4) | 30% | DSPC 50% | 20% |
| No8 (HPX-5) | 30% | DSPC 40% | 30% |
| No9 (HPX-6) | 30% | DPPC 40% | 30% |
| No10 (HPX-7) | 30% | DMPC 40% | 30% |
| No11 (HPX-8) | 30% | DLPC 40% | 30% |
| No12 (HPX-9) | 30% | DDPC 40% | 30% |
| No13 (B-IDM) | 30% | POPC 55% | 15% |
| No14 (HPX-10) | 25% | DMPC 45% | 30% |
| No15 (HPX-11) | 35% | DPPC 45% | 20% |

The liposomal suspensions thus prepared were analyzed in three ways: 1.) by visual observation of the vials, 2.) by visual observation of the liposomes under an optical microscope and 3.) by measurement of the size distribution of the particles. (DTP), by an automated image analysis system.

For this analysis, a 5 μL aliquot is placed between two microscope slides, and several fields are examined for the evaluation of the particle size distribution.

Automated image analysis measures the size of approximately 30,000 liposomal particles for each suspension.

Results: The preparation method makes it possible to obtain translucent and slightly opaque liposomal suspensions, for example FIG. 1 shows a vial containing suspension No. 8.

Figure 2:
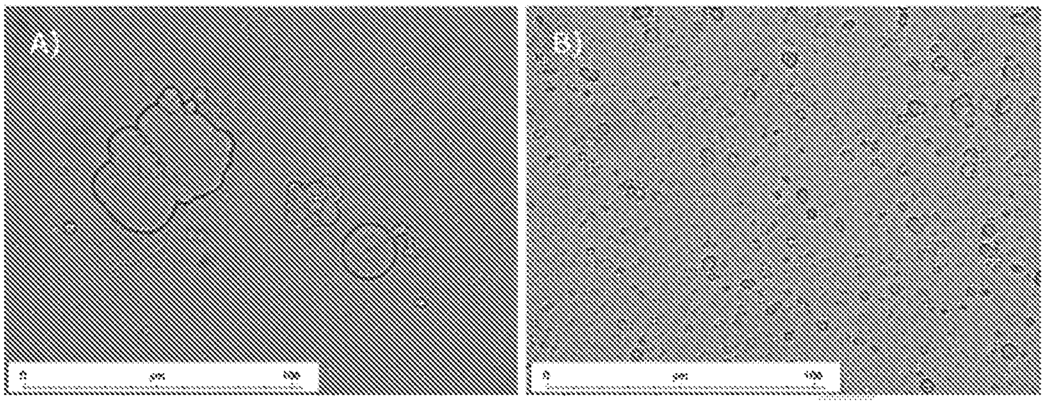
FIG. 2 shows optical microscopy images of liposomes before filtration (image A) and after filtration at 5 μm (image B). The magnification is ×1030.

FIG. 2 shows optical microscopy images of the liposomes of suspension No. 8, before filtration (image A) and after filtration at 5 μm (image B).

The magnification is ×1030.

In FIG. 2, image A shows a liposomal suspension obtained without any filtration.

The liposomes are heterogeneous, without a round shape, and have sizes which can exceed 50 μm.

Image B shows a liposomal suspension after a series of ten filtrations through a 5 μm filter membrane.

In this case, the observed liposomes were much more homogeneous in terms of shape and sizes (less than 10 μm)

Figure 3:
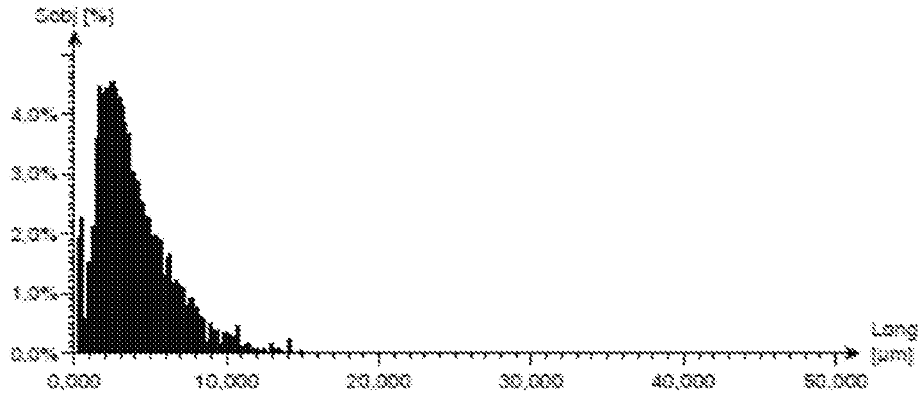
FIG. 3 shows the size distribution of the liposomes obtained by an automated image analysis method.

FIG. 3 gives a typical example of the particle size distribution obtained by the automated image analysis method.

The results of this analysis are characterized by the d10, d50 and d90 values which indicate the maximum size (in pm) reached by 10%, 50 and 90% of the liposomal particles, respectively, of each suspension analyzed.

Table 2 below summarizes the results of these analyzes for the liposome suspensions described in Table 1.

TABLE 2

Table 2

Figure 4:
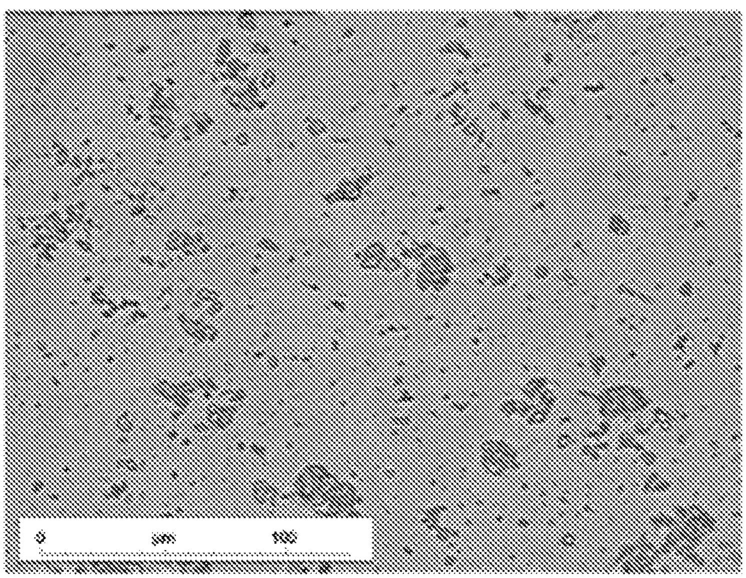
FIG. 4 shows a light microscopy image of liposomes forming aggregates larger than 20 μm.

| Suspension No. (code used in the laboratory) | d50 (μm) | d10 (μm) | d90 (μm) |
|---|---|---|---|
| No1 (Tanguay) | Large aggregates of particles were observed under a microscope. These aggregates had a size greater than 20 μm despite extrusion through a 5 μm filter, as shown in FIG. 4. The presence of these aggregates prevented a meaningful measurement of liposomal particle distribution by image analysis. | | |
| No2 (Mepact) | 3 | 2 | 6 |
| No3 (HPX-0) | 3 | 1 | 6 |
| No4 (HPX-1) | 3 | 1 | 7 |

TABLE 2-continued

| Table 2 | | | |
|---|---|---|---|
| Suspension No. (code used in the laboratory) | d50 (μm) | d10 (μm) | d90 (μm) |
| No5 (HPX-2) No6 (HPX-3) | The manufacture of these suspensions was not feasible since the 5 μm filter was blocked by the suspension, making extrusion impossible. | | |
| No7 (HPX-4) | 5 | 2 | 11 |
| No8 (HPX-5) | 5 | 2 | 10 |
| No9 (HPX-6) | 4 | 2 | 9 |
| No10 (HPX-7) | 3 | 1 | 6 |
| No11 (HPX-8) | 4 | 2 | 7 |
| No12 (HPX-9) | 3 | 2 | 7 |
| No13 (B-IDM) | 4 | 2 | 8 |
| No14 (HPX-10) | 3 | 2 | 7 |
| No15 (HPX-11) | 4 | 2 | 6 |

Observation of vials of liposomal suspensions No. 2, 3, 4, 7, 8, 9, 10, 11, 12, 13, 14 and 15 show translucent, slightly opaque liquids similar to FIG. 1.

Observation under a microscope of these suspensions showed that they were similar to that illustrated in FIG. 2—Image B. These suspensions were the subject of a particle size distribution study by image analysis automated.

The results are shown in Table 2.

These results show that without addition of DOPS, the liposomal particles obtained after extrusion through a 5 μm filter are unstable and spontaneously form large aggregates.

These results also show that the proportion of cholesterol should not exceed 30% since a higher proportion prevents obtaining homogeneous liposomal suspensions.

Example 2: Analysis of the Concentration of MTP-PE

The soluble fraction of MTP-PE (in free form or encapsulated in liposomes) was quantified in each preparation, after dilution of an aliquot in a solvent mixture in order to allow its injection into a chromatography apparatus.

Solution concentration was measured by HPLC. HPLC analysis conditions are summarized in Table 3.

TABLE 3

| | |
|---|---|
| HPLC | Injector & pump: Alliance 2695 Waters<br>Detector: Photo Diode Array 996 Waters<br>Software: Empower Waters |
| Columns | Phenomenex Synergi Polar RP-80 Å<br>150 mm × 4.6 mm − dp = 4 μm |
| Mobile Phase | A: 5 mM NH5CO2 in H2O (20%)<br>B: MeOH (80%)<br>isocratique elution |
| Flux | 1 mL/min |
| Column temperature | 30° C. |
| Detection | UV = 205 nm |
| Standard Solution | For the evaluation of MTP-PE: 1 mg/mL solution in water<br>For calibration: T100% ≈ 10 mg MTP-PE, qs 10 mL water<br>Two independent standard solutions tested<br>Calibration from T5% to T100% |
| Test Solution | Dilution in H2O or H2O/THF (1:1) |
| Injection volume | 10 ou 20 μL |
| Injector temperature | 20° C. |
| Retention time | ≈6.4 min for MTP-PE |

Under these conditions, a retention peak is observed at 6.5 minutes. Analyzes of the peaks of suspensions Nos. 2, 3, 4, 7 and 8 reveal concentrations of 0.08 mg/ml which are consistent with their preparations.

Example 3 Effects of Bile Salts on the Stability of Liposomal MTP-PE Suspensions Liposomal suspensions No. 2, 3, 4, 7, 8, 9, 10, 11, 12, 13, 14 and 15 described in example 1 were exposed to a mixture of bile salts (sodium taurocholate, sodium deoxycholate and sodium cholate hydrate) at a concentration of 4 mM each, at 37° C. and for 3 hours.

Stability was assessed using the methods outlined in Example 1, at T-0 h (immediately after exposure to bile salts), then at T-1 h and T-3 h (after 1 hour and three hours of bile salt exposure, respectively). The results are summarized in Table 4.

TABLE 4

Figure 5:
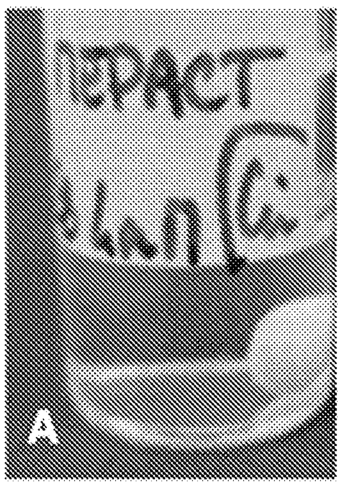
FIG. 5 shows a vial containing a liposome suspension after treatment with bile salts. Observation of the vial shows that the liposomes are denatured and the suspension becomes transparent (Image A)
Figure 5:
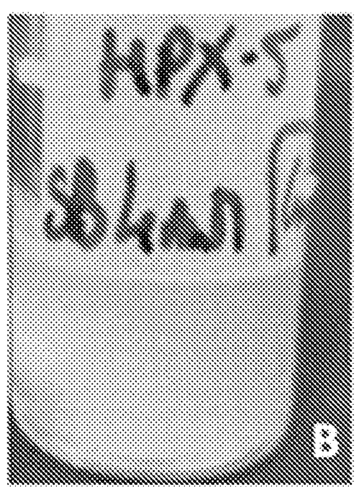

| Suspension No. (code used in the laboratory) | T-0 | T-1 h | T-3 h |
|---|---|---|---|
| No2 (Mepact) No3 (HPX-0) No4 (HPX-1) No 13 (B-IDM) | Observation of the vials that contain these suspensions reveals that they become transparent after a few minutes, as illustrated in FIG. 5 - Image A. Microscopic observation of these liposomal suspensions reveals only tiny liposome debris, making it impossible to analyze the particle size distribution. | | |
| No7 (HPX-4) | d50 = 5<br>d10 = 2<br>d90 = 11 | d50 = 5<br>d10 = 2<br>d90 = 10 | D50 = 5<br>d10 = 2<br>d90 = 5 |
| No8 (HPX-5) | D50 = 5<br>d10 = 2<br>d90 = 10 | D50 = 5<br>d10 = 2<br>d90 = 11 | D50 = 5<br>d10 = 2<br>d90 = 11 |
| No9 (HPX-6) | D50 = 5<br>d10 = 2<br>d90 = 11 | D50 = 4<br>d10 = 2<br>d90 = 10 | D50 = 4<br>d10 = 2<br>d90 = 10 |
| No10 (HPX-7) | D50 = 3<br>d10 = 2<br>d90 = 7 | D50 = 3<br>d10 = 2<br>d90 = 7 | D50 = 3<br>d10 = 1<br>d90 = 6 |
| No11 (HPX-8) | D50 = 3<br>d10 = 1<br>d90 = 7 | D50 = 3<br>d10 = 1<br>d90 = 6 | D50 = 3<br>d10 = 1<br>d90 = 6 |

TABLE 4-continued

Figure 6:
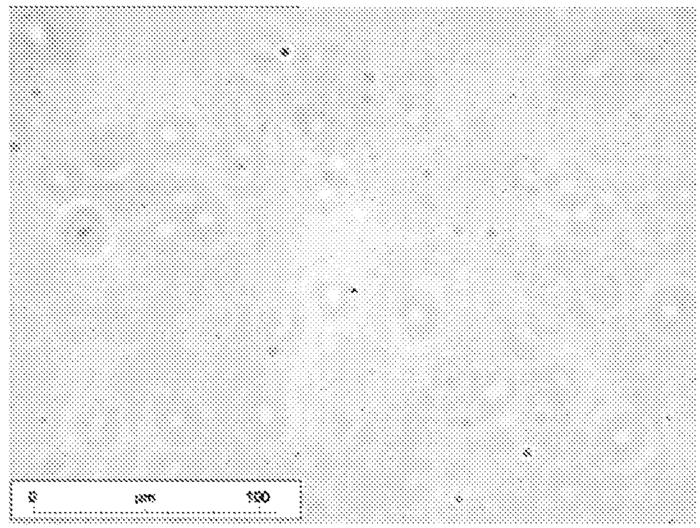
FIG. 6 shows an optical microscope image of a suspension of denatured liposomes.

| Suspension No. (code used in the laboratory) | T-0 | T-1 h | T-3 h |
|---|---|---|---|
| No 12 (HPX-9) | d50 = 3<br>d10 = 1<br>d90 = 7 | Microscopic observation of these liposomal suspensions reveals very small liposomal particles in small quantities, as illustrated in FIG. 6. Size distribution analysis was not possible. | |
| No14 (HPX-10) | D50 = 4<br>d10 = 1<br>d90 = 7 | D50 = 3<br>d10 = 2<br>d90 = 6 | D50 = 3<br>d10 = 1<br>d90 = 6 |
| No15 (HPX-11) | D50 = 4<br>d10 = 2<br>d90 = 7 | D50 = 4<br>d10 = 2<br>d90 = 6 | D50 = 3<br>d10 = 1<br>d90 = 7 |

FIG. 5 shows photographs of vials containing suspension No. 2 on the left (image A) and suspension No. 8 on the right (image B).

These two suspensions were mixed with bile salts.

Suspension No. 2 became limpid and transparent after a few minutes of exposure to bile salts.

On microscopic observation, it was impossible to find liposomes.

Conversely, suspension No. 8 resisted degradation by bile salts.

FIG. 6 shows a photograph taken under an optical microscope of suspension No. 12 after one hour of exposure to bile salts.

The image reveals almost total degradation of the liposomes since only a few debris are visible.

Taken collectively, these results show that liposomal formulations that include DSPC, DPPC, DMPC, or DLPC in place of POPC, as well as 25-35% DOPS and 20-30% cholesterol resist degradation by bile salts for several hours.

Example 4: Effects of Acid pH on the Stability of Liposomal MTP-PE Suspensions Liposomal suspensions No. 2 and No. 8 were exposed for 1 hour at pH 1.

Visual examination of the suspensions in the flasks and under the microscope did not reveal any noticeable degradation effect.

Example 5: Inclusion of MTP-PE in Liposomes

The method was prepared according to the method described in Example No. 1 and using the lipid proportions of solution No. 8.

Different proportions of MTP-PE were added: 0.4%, 1%, 5% and 10%.

Vial and microscopic observation of these suspensions showed liposomal suspensions similar to FIGS. 1 and 2-B. The addition of MTP-PE up to a proportion of 10% therefore does not lead to disorganization of the structure of the liposomes.

Example 6: Manufacture of Liposomal MTP-PE in Dry Powder Form

The dried liposomal particles were prepared using an atomization drying method known as “spray drying.”

The device used was a Büchi mini spray dryer 290.

The atomization drying process involves four steps: atomization of the product in a spray nozzle, air-spray contact, drying of the spray droplets and collection of the solid product.

The method was used according to the proportions of solution No. 8.

The lipids and mifamurtide were dissolved in a mixture of chloroform and methanol (5:1) to the final concentration of 80 μM.

The solution was injected using a 1 mm diameter spray nozzle and a flow rate of 20 ml/minute. The temperature of the drying chamber was 90° C. Spray-dried particles were collected in a tank attached to a cyclone and stored in a refrigerator prior to characterization.

The particles obtained were measured by microscopy and had an average diameter of between 1 and 5 μm.

The dry powder thus obtained was dissolved in an aqueous saline solution (0.9% NaCl). The suspension was shaken manually for a few minutes.

Microscopic observation showed a liposomal suspension composed of particles with an average size of 2 μm, thus demonstrating that the dry powder thus obtained is water-dispersible.

Example 7: Manufacture of Liposomal MTP-PE in Dry Powder Form

Two types of dry liposomal particles were prepared using the method described in Example 5, either by adding mannitol (35 mM) to the starting solution, or without adding any.

The crystallinity of these dry particles prepared with and without mannitol was determined by X-ray diffraction, with a copper source (Philips, XPERT model).

Measurements were made at room temperature using a few milligrams of each sample and a scan rate of 2 degrees per minute.

The results show greater crystallinity for the suspensions prepared without mannitol.

Example 8: Study of the Oral Administration of Liposomal MTP-PE in Mice

Suspensions of liposomal MTP-PE No. 1 and No. 10 were prepared according to the method indicated in example 1.

Additionally, these liposomes were prepared by incorporating 0.5% of a fluorescent label N-4-nitrobenzo-2-oxa-1,3-diazolephosphatidylethanolamine.

A set of 30 BALB/c mice was randomly divided into two Groups A and B of 15 mice. Mice of Group A received an administration of suspension No. 1 by oral gavage at the dose of 20 μg of MTP-PE and mice of Group B were administered suspension No. 10 at the same dose of MTP-PE. Blood samples (approximately 100 μL) were collected at 1, 4, and 24 hours after oral administration (5 mice per group per collection time).

Smear tests were taken from each blood sample.

The smear tests were examined with a fluorescence microscope (Zeiss fluorescence microscope) and the number of fluorescent monocytes was counted for each smear test.

The number of fluorescent monocytes is a marker of the level of liposome absorption, i.e. the transfer of intact and non-destructured liposomes from the lumen of the intestinal tract to the bloodstream.

After passing through the bloodstream, liposomes that have been absorbed are rapidly phagocytosed by circulating monocytes.

The mean number of fluorescent monocytes was 3, 7 and 5 times higher in Group B compared to Group A, at times 1, 4 and 24 hours, respectively.

Example 9: Preclinical Study of Proof of Concept—Therapeutic Efficacy of Liposomal MTP-PE Prepared According to the Invention and Administered Orally in a Kidney Cancer Model The objective of this study was to evaluate the ability of a suspension of liposomal MTP-PE, prepared according to the invention and administered orally, to inhibit the development of lung metastases from kidney cancer.

The experimental model consisted of using immunocompetent mice of the BALB/c strain and transplanting them with RENCA cells of kidney cancer of murine origin under the capsule of one of the two kidneys.

This orthotopic graft forms a syngeneic kidney tumor.

In this model, tumor cells disseminate continuously in the animal's body and form numerous metastases in the lungs after 17 days.

Material and Methods

Suspensions of liposomes were prepared according to the method indicated in example 1.

TABLE 5

| Batch A | Batch B | Batch C |
|---|---|---|
| MTP-PE 1%<br>DSPC 40%<br>DOPS 30%<br>Cholesterol 30% | DSPC 40%<br>DOPS 30%<br>Cholesterol 30% | MTP-PE 1%<br>POPC 100% |

Bile salt resistance tests were carried out according to the method described in Example 3 and showed that Batches A and B are resistant whereas Batch C is rapidly destructured.

The RENCA cell line is derived from a tumor that arose spontaneously as renal cortical adenocarcinoma in BALB/c mice and was provided by the American Type Culture Collection (USA).

The tumor cells were cultured in a monolayer at 37° C. in a humidified atmosphere (5% CO2, 95% air).

The culture medium was RPMI 1640 containing 2 mM L-glutamine supplemented with 10% fetal bovine serum and 0.1 mM non-essential amino acids and 1 mM sodium pyruvate. Tumor cells adhere to plastic vials.

For experimental use, the tumor cells are detached from the culture flask by a 5-minute treatment with trypsin-versene, in Hanks' medium without calcium or magnesium and neutralized by adding complete culture medium.

The cells are then counted and the viability is assessed using a 0.25% trypan blue exclusion test.

Forty healthy female BALB/c mice, 6-7 weeks old on receipt, were obtained from Charles River.

RENCA tumors were induced on day zero (DO) by the orthotopic route in 40 BALB/c female mice under anesthesia. Briefly, the animal's abdomen was opened through a midline incision under aseptic conditions.

A total of 500,000 RENCA tumor cells in 25 μL of RPMI medium were slowly injected into the subcapsular space of the right kidney.

Animals were randomized based on their individual body weight on Day −2.

The animals were randomized into four groups of ten animals each (Group 1, Group 2, Group 3 and Group 4.) The homogeneity of body weight between the groups was tested by an analysis of variance (ANOVA).

Animals of Group 1 animals were untreated.

Animals of Groups 2, 3 and 4 were treated with Batchs B, A and C, respectively. The treatments were administered on Days 0, 3, 5, 7, 9, 11, 13, 15 and 17. Treatment was administered by oral gavage using a gavage tube. The volume of administration was 5 ml/kg adjusted to the most recent individual body weight. In Groups 3 and 4, the dose of MTP-PE was 1 mg/kg.

All animals were euthanized by deep isoflurane gas anesthesia on Day 17, one hour after treatment.

A blood sample of 500 μL was taken by intracardiac puncture.

Blood was collected in collection tubes with an anticoagulant (lithium heparin).

The pipes were centrifuged (2000 g, 10 minutes, 4° C.) to obtain the plasma and the cell pellet. Plasma from each animal was aliquoted and stored in two propylene tubes (approximately 125 μL/tube) at −80° C. to assess plasma levels of liposomal MTP-PE according to the method described in the publication Venkatakrishnan et al. British Journal of Clinical Pharmacology 77(6): 986-97, 2014). The cell pellet from each animal was transferred and stored in a propylene tube at −80° C. for further analysis.

Lung pairs from all mice were removed and weighed.

Lung weight reflects the total amount of lung metastases. In addition, a macroscopic enumeration of lung metastases on each lung was performed in all mice. The lungs were then fixed in 4% neutral buffered formalin for 24-48 h and then embedded in paraffin (Histowax®, Histolab, Sweden). Samples were stored at room temperature for further microscopic analysis.

Results

The results of the lung metastasis counts are summarized in Table 6.

TABLE 6

| | Groupe 1 | Groupe 2 (Batch B) | Groupe 3 (Batch A) | Groupe 4 (Batch C) |
|---|---|---|---|---|
| MTP-PE (mg/kg) | No treatment | 0 | 1 | 1 |
| Type of liposomes | | Resistant to bile salts | Resistant to bile salts | Degraded by bile salts |
| Total number of mice | 10 | 10 | 10 | 10 |
| Mice with more than 400 metastases | 7 | 7 | 3 | 7 |

TABLE 6-continued

| | Groupe 1 | Groupe 2 (Batch B) | Groupe 3 (Batch A) | Groupe 4 (Batch C) |
|---|---|---|---|---|
| Mice with between 100 and 400 metastases | 3 | 3 | 1 | 2 |
| Mice with less than 100 metastases | 0 | 0 | 6 | 1 |
| Median number of metastases per mouse | >400 | >400 | 72 | >400 |

These results show a significant reduction in the number of lung metastases in Group 3 compared to Groups 1, 2 and 4.

Results for lung weight are summarized in Table 7.

TABLE 7

| | Groupe 1 | Groupe 2 (Batch B) | Groupe 3 (Batch A) | Groupe 4 (Batch C) |
|---|---|---|---|---|
| MTP-PE (mg/kg) | No treatment | 0 | 1 | 1 |
| Type of liposomes | | Resistant to bile salts | Resistant to bile salts | Degraded by bile salts |
| Total number of mice | 10 | 10 | 10 | 10 |
| Average lung weight (g) | 0.55 | 0.73 | 0.35 | 0.67 |
| 95% confidence interval | 0.27 | 0.29 | 0.25 | 0.25 |
| Median lung weights | 0.58 | 0.85 | 0.15 | 0.87 |

These results showed a significant reduction in lung weight in Group 3 compared to Groups 1, 2 and 4.

This reduction was statistically significant ($p<0.05$, Student's t-test) compared to Groups 2 and 4.

Plasma levels of liposomal MTP-PE were also significantly higher in Group 3 compared to Groups 2 and 4.

Conclusion

These results demonstrate the ability of MTP-PE to inhibit the metastatic spread of a cancerous tumor when it is formulated in liposomes prepared according to the invention and administered orally.

These results also demonstrate that a suspension of liposomes prepared according to the invention and without addition of MTP-PE does not have this capacity.

These results also show that MTP-PE formulated in liposomes which are destructured in the presence of bile salts does not have this capacity.

In a published study with a mouse model also using RENCA cells (S. Tanguay et al., Cancer Res.

1994 Nov. 15; 54(22):5882-8), the in vivo anticancer activity of MTP-PE formulated with phosphatidylcholine liposomes and administered orally to mice showed moderate anticancer activity. The experimental conditions used in our model were much more severe. Indeed, in Tanguay's study, a maximum quantity of 25,000 RENCA cells had been injected once intravenously into the mice. In our model, a quantity of 500,000 cells was grafted into a kidney of the animals and these cells constituted a renal tumor in each animal. In Tanguay's study, the maximum quantity of pulmonary metastases was 150, whereas this quantity exceeded 400 in our model.

Thus, under our experimental conditions which reflect a much more severe metastatic cancer disease, MTP-PE formulated in bile salt degraded liposomes (Group 4) did not show antimetastatic activity.

Example 10: Preclinical Study of Proof of Concept—Therapeutic Efficacy of Liposomal MTP-PE Prepared According to the Invention and Administered Orally in a Model of Osteosarcoma (Bone Cancer)

The objective of this study was to evaluate the ability of a suspension of liposomal MTP-PE, prepared according to the invention and administered orally, to inhibit the development of pulmonary metastases from bone cancer.

The experimental model consisted of using immunocompetent mice of the C57BL/6 strain and grafting them with MOS-J osteosarcoma cells of murine origin by paratibial intramuscular injection, thus reproducing the human disease.

This orthotopic graft forms an osteolytic bone tumor.

In this syngeneic model, tumor cells disseminate continuously in the animal's body and form metastases in the lungs after 5 weeks.

Suspensions of liposomes were prepared according to the method indicated in example 1.

| Batch D2 | Batch E2 | Batch F2 (Mepact ®) |
|---|---|---|
| MTP-PE 1%<br>DMPC 45%<br>DOPS 30%<br>Cholesterol 25% | DMPC 45%<br>DOPS 30%<br>Cholesterol 25% | MTP-PE 1%<br>POPC 70%<br>DOPS 30% |

Bile salt resistance tests were carried out according to the method described in Example 3 and showed that Batches D2 and E2 are resistant whereas Batch F2 is rapidly destructured.

The MOS-J cell line is derived from a mouse bone tumor and was provided by the Jackson Laboratory (USA).

The tumor cells were cultured in a monolayer at 37° C. in a humidified atmosphere (5% CO2, 95% air).

The culture medium was RPMI 1640 supplemented with 5% fetal bovine serum.

Fifty C57Bl/6 mice, 5-6 weeks old on receipt, were obtained from Charles River.

Bone tumors were induced by paratibial intramuscular injection of 3,000,000 MOS-J cells per mouse.

The animals were randomized two days later according to their individual body weights into 5 groups of ten animals each (Group 1, Group 2, Group 3, Group 4 and Group 5)

Animals of Group 1 were untreated.

Animals of Groups 2, 3 and 4 were treated with Batchs E2, D2 and F2, respectively.

Animals of Group 5 were treated with an aqueous solution of MTP-PE. The treatments were administered orally two to three times per week.

In Groups 3, 4 and 5, the dose of MTP-PE was 1 mg/kg.

All animals were euthanized after 5 weeks and the number of lung metastases was counted using a binocular loupe.

The results showed that there were between 0 and 7 pulmonary metastases per mouse in Group 2, while this number varied between 6 and 23 in the other Groups.

These results therefore showed an antimetastatic effect of MTP-PE when this compound is formulated in the form of liposomes resistant to bile salts and administered orally.

Example 11: Preclinical Study of Proof of Concept—Therapeutic Efficacy of the Liposomal MTP-PE Prepared According to the Invention and Administered Orally in a Breast Cancer Model The objective of this study was to evaluate the capacity of a suspension of liposomal MTP-PE, prepared according to the invention and administered orally, to inhibit the development of pulmonary metastases from cancer of the mammary gland.

The experimental model consisted of using immunocompetent mice of the BALB/c strain and performing an orthotopic transplant of 4T-1 cells of mammary cancer of murine origin.

This orthotopic graft forms a tumor reproducing human breast cancer which disseminates and forms metastases in the lungs after 3 weeks.

Suspensions of liposomes were prepared according to the method indicated in example 1.

| Batch G3 | Batch H3 (Control) |
|---|---|
| MTP-PE 0.5%<br>DPPC 45%<br>DOPS 27%<br>Cholesterol 28% | DPPC 45%<br>DOPS 27%<br>Cholesterol 28% |

The 4T1 cell line is derived from mouse mammary tumor and was provided by ATCC (USA). The tumor cells were cultured in a monolayer at 37° C. in a humidified atmosphere (5% CO2, 95% air).

The culture medium was RPMI 1640 supplemented with 5% fetal bovine serum.

4T1 tumors were induced on day zero (DO) orthotopically in 60 BALB/c female mice under anesthesia.

A total of 300,000 4T1 tumor cells were slowly injected into the right thoracic breast tissue.

Animals were randomized by tumor size on Day 9 into six groups of ten animals each (Groups 1, 2, 3, 4, and 5). Homogeneity of tumor sizes between groups was tested by analysis of variance (ANOVA).

The animals of Groups 1, 2 and 3 were treated respectively with Batch H3 (control), Batch G3 and Batch G3 twice a week orally.

Additionally, animals in Groups 2 and 4 were treated with intravenous injections of doxorubicin at 8 mg/kg once weekly for 3 weeks. Animals in Groups 3 and 5 were treated with intraperitoneal injections of an anti-PD-L1 monoclonal antibody twice a week for 3 weeks. All animals were euthanized after 3 weeks. The number of lung metastases was counted using a binocular loupe.

The results showed that there were between 10 and 30 lung metastases in Groups 1, 4 and 5 while metastases were significantly reduced in Groups 2 and 3. Chemotherapy (doxorubicin) and immunotherapy (anti PD-L1) treatments did not show significant efficacy in this model. On the other hand, the number of metastases was greatly reduced when the animals received a combination of chemotherapy or immunotherapy, in combination with MTP-PE formulated in the form of bile salt-resistant liposomes and administered orally.

The invention claimed is:

1. An oral liposomal composition for oral administration, the composition comprising:

a) from 0.1 to 10% by weight of muramyl tripeptide phosphatidyl ethanolamine (MTP-PE) relative to the weight of the liposomal composition; and b) a liposome comprising:

i) from 25% to 35% by weight of di-oleoyl-phosphatidylserine (DOPS) relative to the total weight of the liposome, ii) from 30% to 50% by weight of 1,2-distearoyl-sn-glycero-3-phosphocholine (DSPC), 1,2-dihexadecanoyl-sn-glycero-3-phosphocholine (DPPC), di-myristoyl-phosphatidyl-choline (DMPC), or di-linoleoyl-phosphatidyl-choline (DLPC), relative to the total weight of the liposome, and iii) from 20% to 30% by weight of cholesterol, relative to the total weight of the liposome, wherein the liposomal composition is stable in the presence of bile salts.

2. The oral liposomal composition according to claim 1, wherein the composition is a pharmaceutical composition.

3. The oral liposomal composition according to claim 1, wherein the composition is in form of a dry powder, wherein the composition optionally comprises at least one pharmaceutically acceptable excipient.

4. The oral liposomal composition according to claim 1, wherein the liposomal composition comprises:

a) 1% by weight of MTP-PE, and b) a liposome consisting of:

i) 30% by weight of DOPS relative to the total weight of the liposome, ii) 40% by weight of DSPC relative to the total weight of the liposome, and, iii) 30% by weight of cholesterol relative to the total weight of the liposome.

5. The oral liposomal composition according to claim 1, wherein the liposomal composition is stable at a pH of 1 for one hour.

* * * * *